(12) United States Patent
Wang et al.

(10) Patent No.: US 6,444,761 B1
(45) Date of Patent: Sep. 3, 2002

(54) WATER-SOLUBLE ADHESIVE COMPOSITIONS

(75) Inventors: James Hongxue Wang, Appleton; Bridget Golden, Fond du Lac, both of WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/474,041

(22) Filed: Dec. 28, 1999

(51) Int. Cl.⁷ ............................................. C08F 283/06
(52) U.S. Cl. ..................................................... 525/404
(58) Field of Search ........................................ 525/404

(56) References Cited

U.S. PATENT DOCUMENTS

| | | |
|---|---|---|
| RE25,880 E | 10/1965 | Cline |
| 3,340,327 A | 9/1967 | Spellberg |
| 3,546,321 A * | 12/1970 | Jabloner et al. ............ 525/404 |
| 3,670,731 A | 6/1972 | Harron |
| 3,867,324 A | 2/1975 | Clendinning |
| 3,891,584 A * | 6/1975 | Ray-Chaudhuri et al. ... 525/404 |
| 4,032,993 A | 7/1977 | Coquard et al. |
| 4,161,468 A * | 7/1979 | Davis et al. ................. 525/404 |
| 4,229,334 A | 10/1980 | Klabacka et al. |
| 4,496,619 A | 1/1985 | Okamoto |
| 4,511,687 A | 4/1985 | Nakanishi |
| 4,564,648 A * | 1/1986 | Huybrechts et al. ........ 525/404 |
| 4,585,835 A | 4/1986 | Saegusa |
| 4,594,389 A | 6/1986 | Lal |
| 4,617,235 A | 10/1986 | Shinonome et al. |
| 4,627,950 A | 12/1986 | Matsui et al. |
| 4,795,668 A | 1/1989 | Krueger et al. |
| 4,857,602 A | 8/1989 | Casey |
| 4,966,808 A | 10/1990 | Kawano |
| 5,011,892 A * | 4/1991 | Engelhardt et al. ......... 525/404 |
| 5,097,004 A | 3/1992 | Gallagher et al. |
| 5,097,005 A | 3/1992 | Tiez |
| 5,109,075 A * | 4/1992 | Yu ............................. 525/404 |
| 5,216,050 A | 6/1993 | Sinclair |

(List continued on next page.)

FOREIGN PATENT DOCUMENTS

| | | |
|---|---|---|
| DE | 2513251 | 9/1976 |
| EP | 0080274 | 6/1983 |
| EP | 0210754 | 2/1987 |
| EP | 0436966 | 7/1991 |
| EP | 0438598 | 7/1991 |
| EP | 503608 * | 9/1992 |
| EP | 0612773 | 8/1994 |
| EP | 0648871 | 4/1995 |
| EP | 0705934 | 4/1996 |
| EP | 0761795 | 3/1997 |
| EP | 0781538 | 7/1997 |
| JP | 61-181859 | 8/1986 |
| JP | 5-125123 | 5/1993 |
| WO | 93/07199 | 4/1993 |
| WO | 94/17226 | 8/1994 |
| WO | 95/10645 | 4/1995 |
| WO | 95/18191 | 7/1995 |
| WO | 96/20738 | 7/1996 |
| WO | 97/02375 | 1/1997 |
| WO | 98/36117 | 8/1998 |

OTHER PUBLICATIONS

Derwent Publications Ltd., Database WPI, JP 08 212995 (Misubishi Paper Mills Ltd.), Aug. 20, 1996.
Patent Abstracts of Japan, JP 06–207324(Unitika Ltd.), Jul. 26, 1994.
Derwent Publications Ltd., Database WPI, JP 01 246411 (Sawashita A), Oct. 2, 1989.

*Primary Examiner*—Philip Tucker
(74) *Attorney, Agent, or Firm*—Kilpatrick Stockton LLP

(57) ABSTRACT

Water-soluble adhesive compositions based on novel poly (ethylene oxide) compositions are disclosed. The poly (ethylene oxide) compositions are grafted with a nonpolar monomer and have improved melt processability and properties that make the poly(ethylene oxide) compositions desirable for water-soluble and hot-melt adhesive applications.

28 Claims, 1 Drawing Sheet

U.S. PATENT DOCUMENTS

| | | |
|---|---|---|
| 5,217,495 A | 6/1993 | Kaplan et al. |
| 5,217,798 A * | 6/1993 | Brady et al. ............... 525/404 |
| 5,219,646 A | 6/1993 | Gallagher et al. |
| 5,225,491 A * | 7/1993 | Yu ........................... 525/404 |
| 5,264,491 A | 11/1993 | Quirk |
| 5,304,420 A | 4/1994 | Hirakawa et al. |
| 5,366,804 A | 11/1994 | Dugan |
| 5,407,442 A | 4/1995 | Karapasha |
| 5,442,016 A | 8/1995 | Jarrett |
| 5,453,144 A * | 9/1995 | Kauffman ................. 156/213 |
| 5,466,410 A | 11/1995 | Hills |
| 5,470,941 A | 11/1995 | Kim et al. |
| 5,476,909 A | 12/1995 | Kim |
| 5,514,380 A | 5/1996 | Song |
| 5,519,085 A | 5/1996 | Ma |
| 5,522,841 A | 6/1996 | Roby |
| 5,530,074 A | 6/1996 | Jarrett |
| 5,589,545 A | 12/1996 | Ramachandran |
| 5,618,911 A | 4/1997 | Kimura |
| 5,685,757 A | 11/1997 | Kirsch et al. |
| 5,698,322 A | 12/1997 | Tsai et al. |
| 5,700,872 A | 12/1997 | Wang et al. |
| 6,117,947 A * | 9/2000 | Wang et al. ............... 525/404 |
| 6,166,149 A * | 12/2000 | Yamaguchi et al. ........ 525/404 |

* cited by examiner

WATER-SOLUBLE ADHESIVE COMPOSITIONS

FIELD OF THE INVENTION

The present invention is directed to graft copolymers of poly(ethylene oxide) and at least one nonpolar monomer. The graft copolymers of poly(ethylene oxide) and nonpolar monomer described herein are useful as water-soluble adhesives and as components of water-soluble adhesives.

BACKGROUND OF THE INVENTION

Disposable personal care products such as pantiliners, diapers, tampons etc. are a great convenience. Such products provide the benefit of one time, sanitary use and are convenient because they are quick and easy to use. However, disposal of such products is a concern due to limited landfill space. Incineration of such products is not desirable because of increasing concerns about air quality and the costs and difficulty associated with separating such products from other disposed, non-incineratable articles. Consequently, there is a need for disposable products which may be quickly and conveniently disposed of without dumping or incineration.

It has been proposed to dispose of such products in municipal and private sewage systems. Ideally, such products would be flushable and degradable in conventional sewage systems. Products suited for disposal in sewage systems and that can be flushed down conventional toilets are termed "flushable". Disposal by flushing provides the additional benefit of providing a simple, convenient and sanitary means of disposal. Personal care products must have sufficient strength under the environmental conditions in which they will be used and be able to withstand the elevated temperature and humidity conditions encountered during use and storage yet still lose integrity upon contact with water in the toilet. Therefore, a water-disintegratable material having mechanical integrity when dry is desirable.

Due to its unique interaction with water and body fluids, poly(ethylene oxide) (hereinafter PEO) is currently being considered as a component material for water-disintegratable films, fibers, and flushable products. PEO,

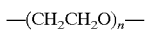

is a commercially available water-soluble polymer that can be produced from the ring opening polymerization of the ethylene oxide.

Because of its water-soluble properties, PEO is desirable for flushable applications. However, there is a dilemma in melt processing PEO. Low molecular weight PEO resins have desirable melt viscosities and melt pressure properties for melt processing but have limited solid state properties when melt processed into structural articles such as films.

A commercial example of a low molecular weight PEO resin is POLYOX® WSR N-80 PEO which is commercially available form Union Carbide. POLYOX® WSR N-80 PEO has an approximate molecular weight of 200,000 g/mol as determined by Theological measurements. As used herein, low molecular weight PEO compositions are defined as PEO compositions with an approximate molecular weight of less than and including about 200,000 g/mol.

In personal care product industry, flushable thin-gauged films and melt-spun fibers are desired for commercial viability and ease of disposal. The low melt strength and low melt elasticity of low molecular weight PEO limit the ability of the low molecular weight PEO to be drawn into films having a thickness of less than about 1.25 mil. Although low molecular weight PEO can be thermally processed into films, thin-gauged films of less than about 1 mil in thickness cannot be obtained due to the lack of melt strength and melt elasticity of the low molecular weight PEO. Efforts have been attempted to improve the processability of PEO by blending the PEO with a second polymer, a copolymer of ethylene and acrylic acid, in order to increase the melt strength. The PEO/ethylene acrylic acid copolymer blend is able to be processed into films of about 1.2 mils in thickness. However, the blend and resulting film are not water-soluble, especially at high levels of ethylene acrylic acid copolymer, i.e. about 30 weight percent. More importantly, thin films made from low molecular weight PEO are too weak and brittle to be useful for personal care applications. Low molecular weight PEO films have low tensile strength, low ductility, and are too brittle for commercial use. Further, films produced from low molecular weight PEOs become brittle during storage at ambient conditions. Such films shatter and are not suited for commercial applications.

High molecular weight PEO resins are expected to produce films with improved mechanical properties compared to films produced from low molecular weight PEO resins. An example of a high molecular weight PEO is POLYOX® WSR 12K PEO which is commercially available from Union Carbide. POLYOX® WSR 12K PEO has a reported approximate molecular weight of 1,000,000 g/mol as determined by Theological measurements. As used herein, high molecular weight PEOs are defined as PEOs with an approximate molecular weight of greater than and including about 300,000 g/mol.

High molecular weight PEOs have poor processability due to their high melt viscosities and poor melt drawabilities. Melt pressure and melt temperature are significantly elevated during melt extrusion of high molecular weight PEOs. During extrusion of high molecular weight PEOs, severe melt fracture is observed. Only very thick sheets can be made from high molecular weight PEOs. High molecular weight PEOs cannot be thermally processed into films of less than about 3–4 mil in thickness. High molecular weight PEOs suffer from severe melt degradation during extrusion and melt processing. This results in breakdown of the PEO molecules and formation of bubbles in the extrudate. The inherent deficiencies of high molecular weight PEOs make it impossible to utilize high molecular weight PEOs in film applications. Even the addition of high levels of plasticizer to the high molecular weight PEOs do not improve the melt processabilities sufficiently to allow the production of thin films without melt fracture and film breakage occurring. In addition, the use of plasticizer in films causes latent problems due to migration of the plasticizer to the film surface.

There is also a dilemma in utilizing PEO in the fiber-making processes. PEO resins of low molecular weights, for example 200,000 g/mol have desirable melt viscosity and melt pressure properties for extrusion processing but cannot be processed into fibers due to their low melt elasticities and low melt strengths. PEO resins of higher molecular weights, for example greater than 1,000,000 g/mol, have melt viscosities that are too high for fiber-spinning processes. These properties make conventional PEOs difficult to process into fibers using conventional fiber-making processes.

PEO melt extruded from spinning plates and fiber spinning lines resists drawing and is easily broken. PEO resins do not form thin diameter fibers using conventional melt fiber-making processes. Conventional PEO resins can only be melt processed into strands with diameters in the range of several millimeters. Therefore, PEO compositions with appropriate melt viscosities for processing fibers and with greater melt elasticities and melt strengths are desired.

In the personal care industry, flushable melt-spun fibers are desired for commercial viability and ease of disposal. PEO fibers have been produced by a solution spinning process. However, it has not been possible to melt process PEO fibers using conventional fiber making techniques such as melt spinning. Melt processing techniques are more desirable than solution casting because melt processing techniques are more efficient and economical. Melt processing of fibers is needed for commercial viability. Prior art PEO compositions cannot be extruded into the melt with adequate melt strength and elasticity to allow attenuation of fibers. Presently, fibers cannot be produced from conventional PEO compositions by melting spinning. There is a need for water-soluble, constructive adhesive compositions comprising PEO that can be used to bond components of flushable articles such as films, non-woven webs elastics, etc. Water-soluble adhesives are desirable in the construction of flushable, personal care articles such as diapers, pantiliners, training pants, adult incontinence products, etc. and in the construction of disposable health care articles such as surgical gowns and masks, wound dressing, bandages, etc.

Currently available PEO resins are not practical for melt processing, thin films, fibers or personal care applications The present inventors have developed novel PEO resins that are practical for melt processing into films and fibers. There is now a need for water-soluble adhesives that are compatible with and can be used in conjunction with these novel PEO resins. Therefore, it is an object of the present invention to provide water-soluble adhesives and a method of making such adhesives.

SUMMARY OF THE INVENTION

Unique graft copolymers of ethylene oxide are disclosed herein. The graft copolymers comprise a backbone of a polymer of ethylene oxide and side chains or branches comprising units of one or more grafted nonpolar monomers. The backbone of the graft copolymers comprises a homopolymer of ethylene oxide but may contain minor amounts of other species. Graft copolymers comprising a backbone of ethylene oxide homopolymer and grafts of nonpolar species can be exemplified by the formula

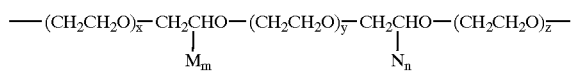

where M and N are the nonpolar, monomeric species that are grafted to the ethylene oxide homopolymer backbone and m, n, x, y and z are positive integers. The graft copolymers of the present invention may have a minor amount of a species other than ethylene oxide in the backbone and may or may not be conterminously grafted with the nonpolar grafting species. The graft copolymers disclosed herein have been found to have properties that make them desirable as water-soluble adhesives and as components in water-soluble and water-responsive adhesives.

Water-soluble resins are desirable for flushable applications. Low molecular weight PEO resins, about 200,000 g/mol or less as determined by Theological measurements that are both thermoplastic and water-soluble resins are commercially available. However, commercially available PEO resins are difficult to process thermoplastically, particularly at higher molecular weights. Due to their poor melt strength, conventional PEO resins cannot be readily processed into films of less than 1 mil thickness even with the addition of processing aids such as plasticizers. Films produced from conventional PEO resins are too weak and too brittle for most commercial applications. A reactive-extrusion method for modifying PEO resins was developed by Wang et al. to overcome the deficiencies of commercially available PEO resins. The reactive-extrusion process developed by Wang et al. is based on the grafting of polar monomers onto PEO, to form polar grafted PEO compositions. The process developed by Wang et al. is disclosed in U.S. application Ser. No. 09/002,197, the disclosure of which is incorporated herein in its entirety. The initial experiments with polar monomers disclosed in U.S. application Ser. No. 09/002,197 establish grafting technology is a valid method to improve both the melt and solid state properties of PEO. The present invention discloses a further improvement in PEO grafting technology and includes the grafting of PEO with nonpolar monomers for water-soluble adhesive applications.

In the present invention, it was discovered that the properties of PEO change dramatically when PEO is grafted with nonpolar monomers. The change in properties is surprisingly more dramatic than in the case of grafting with polar monomers in terms of the reduction of the melt viscosity. The change in melt viscosity is so substantial that the nonpolar monomer grafted PEO resins exhibit properties desirable for hot-melt adhesives. Because PEO resins that are water soluble and can be modified by the methods described herein, the present invention provides modified PEO compositions suitable for use as water-soluble, hot-melt adhesives. Water-responsive adhesives, more particularly water-soluble adhesives, are desirable for flushable product applications but are not readily available commercially. It is demonstrated herein that nonpolar monomer grafted PEO compositions can be used as water-soluble adhesives for bonding water-responsive films, water-responsive nonwovens and water-responsive film/nonwoven laminates. The adhesive compositions comprising nonpolar monomer grafted PEO disclosed in the present invention are useful as components in flushable diapers, pantiliners, training pants, feminine pads, etc. By properly adjusting the adhesive compositions disclosed herein such as by adding tackifiers and waxes, a wide range of hot-melt adhesive compositions can be produced from the nonpolar monomer grafted PEO compositions of the present invention.

DETAILED DESCRIPTION

Figure 1:
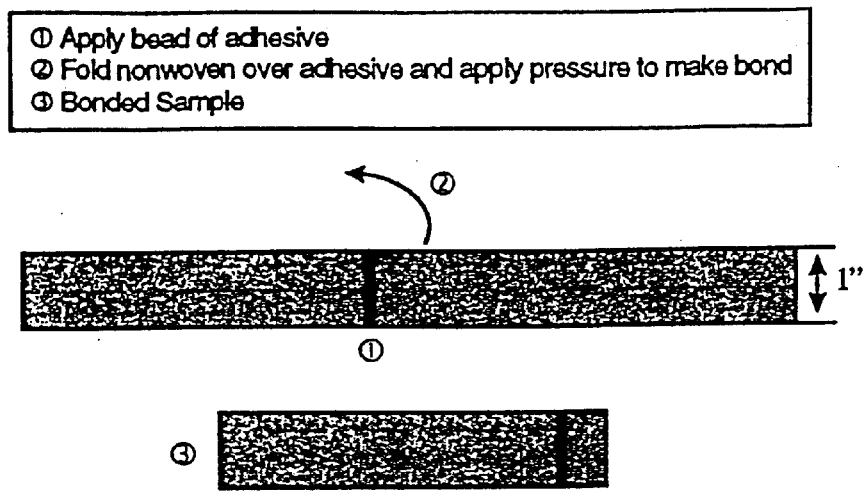
FIG. 1 illustrates the method used to prepare samples for testing the adhesive bond strength of the nonpolar monomer grafted poly(ethylene oxide) compositions.

Water-soluble adhesive compositions can be produced from commercially available poly(ethylene oxide) resins when modified in accordance with the invention disclosed herein. It has been discovered that by grafting water-soluble PEO resins with nonpolar monomers one can produce modified PEO resins with significantly reduced viscosity and desirable adhesive properties that still retain their water solubility. One commercial supplier of several water-soluble PEO resins that can be modified in accordance with the invention is Union Carbide Corporation of Danbury, Conn. Union Carbide sells several water-soluble PEO resins under the trade names POLYOX® and UCARFLOC®. The PEO resins available from Union Carbide are ungrafted homopolymers of ethylene oxide. PEO resins useful for modification include, but are not limited to, ungrafted PEO resins having initial reported approximate molecular weights ranging from about 100,000 g/mol to about 8,000,000 g/mol as determined by Theological measurements by Union Carbide. Several water-soluble PEO resins are listed and described in POLYOX®: Water Soluble Resins, Union Carbide Chemicals & Plastic Company, Inc., 1991 which is incorporated by reference herein in its entirety. Commercially available grades of PEO resin supplied by Union Carbide having average molecular weights with the above range include, but are not limited to, POLYOX® WSR N-750, WSR N-3000, WSR-3333, WSR-205, WSR-N-12K, WSR-N-60K, WSR-301, WSR Coagulant, WSR-303 and WSR N-80. Other PEO resins available from Union Carbide or other suppliers that are water soluble may also be suitable for modification in accordance with the present invention.

Both PEO powder and pellets of PEO can be used in this invention since the physical form of PEO does not affect its behavior in the melt state for grafting reactions. This invention has been demonstrated by the use of PEO in powder form as supplied by Union Carbide. However, PEO resins obtained from other suppliers may be in other forms, such as pellets, and can be modified in accordance with the present invention. The PEO resins and the modified PEO compositions of the present invention may optionally contain various additives such as plasticizers, processing aids, rheology modifiers, antioxidants, UV light stabilizers, pigments, colorants, slip additives, antiblock agents, etc. which may be added before or after grafting of the PEO resin.

A variety of nonpolar monomers may be useful in the practice of this invention. The term "monomer(s)" as used herein includes monomers, oligomers, polymers, mixtures of monomers, oligomers and/or polymers, and any other reactive chemical specie which is capable of covalent bonding with the parent polymer, PEO. Ethylenically unsaturated monomers, i.e. vinyl monomers, not containing a polar functional group, such as hydroxyl, carboxyl, amino, halo, thiol, sulfonic, sulfonate, etc. are appropriate for this invention and are desired. Suggested vinyl nonpolar monomers include styrene and various nonpolar acrylates and nonpolar methacrylates,. Desired vinyl nonpolar monomers include, but are not limited to, acrylates and methacrylates containing one or more alkyl side groups and can be exemplified by the formula

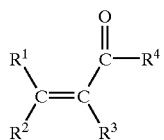

where $R^1$, $R^2$, $R^3$ and $R^4$ can each independently be a nonpolar group including, but not limited to: hydrogen, linear alkyl, branched alkyl, cycloalkyl, and halogen. Desirable nonpolar acrylates and methacrylates include but are not limited to, $C_3$ to $C_{20}$ alkyl acrylates and $C_3$ to $C_{20}$ alkyl methacrylates including cycloalkyl acrylates and cycloalkyl methacrylates and further include substituted alkyl acrylates and methacrylates and substituted cycloalkyl acrylates and methacrylates. Suggested nonpolar monomers include methyl acrylate, ethyl acrylate, propyl acrylate, isopropyl acrylate, butyl acrylate, n-butyl acrylate, sec-butyl acrylate, tert-butyl, pentyl acrylate, hexyl acrylate, 2-ethylhexyl acrylate, heptyl acrylate, octyl acrylate, nonyl acrylate, decyl acrylate, undecyl acrylate, dodecyl acrylate, tridecyl acrylate, tetradecyl acrylate, pentadecyl acrylate, hexadecyl acrylate, heptadecyl acrylate, octadecyl acrylate, methyl methacrylate, ethyl methacrylate, propyl methacrylate, isopropyl methacrylate, butyl methacrylate, n-butyl methacrylate, sec-butyl methacrylate, tert-butyl, pentyl methacrylate, hexyl methacrylate, 2-ethylhexyl methacrylate, heptyl methacrylate, octyl methacrylate, nonyl methacrylate, decyl methacrylate, undecyl methacrylate, dodecyl methacrylate, tridecyl methacrylate, tetradecyl methacrylate, pentadecyl methacrylate, hexadecyl methacrylate, heptadecyl methacrylate, octadecyl methacrylate, etc. The present invention has been demonstrated by the use of 2-ethylhexyl methacrylate (abbreviated as EHMA hereinafter) as the nonpolar monomer that is grafted to the PEO resin for water-soluble adhesive for water-soluble adhesive applications. One embodiment uses acrylates and methacrylates containing aromatic and phenyl rings and groups as the nonpolar monomer. Nonpolar, vinyl monomers comprising aromatic that are desirable include, but are not limited to, nonpolar monomers comprising benzene rings such as benzyl acrylate, benzyl methacrylate, phenylpropyl acrylate, phenylpropyl methacrylate and the like. Another embodiment of the present invention includes mixtures of two or more of the above described monomers grafted to the PEO to provide balanced physical properties and processability.

The EHMA monomer used in the Examples was obtained from Aldrich Chemical Company of Milwaukee, Wis. It is expected that a wide range of nonpolar vinyl monomers, several of which are listed above, would be capable of imparting similar effects as EHMA to PEO and would be effective monomers for grafting and producing adhesive resins. The amount of nonpolar vinyl monomer grafted to the PEO resin can vary. A suggested weight range of nonpolar monomer that can be grafted to the PEO includes from about 0.1 to about 20 weight percent of nonpolar monomer to the weight of PEO resin. Thus, the nonpolar vinyl monomer is added to the poly(ethylene oxide) in a range of from about 0.1 weight percent to about 20 weight percent relative to the weight of the poly(ethylene oxide). Desirably, the amount of nonpolar monomer should exceed 0.1 weight percent in order to sufficiently improve the processability of the PEO. A range of grafting levels of form about 1 percent to about 5 percent is demonstrated in the Examples below.

This invention has been demonstrated by a reactive extrusion process. The grafting of the PEO can also be performed by other processes and with other reaction devices as long as the necessary mixing of the PEO resin, the nonpolar vinyl monomer and other reactive ingredients such as an initiator is achieved and enough thermal energy is provide to effect the grafting reactions between the nonpolar monomer or mixture of monomers and the PEO. For example, the invention may be practiced by using styrene as the nonpolar monomer.

A variety of initiators may be useful in the practice of this invention. When grafting is achieved by the application of heat, as in a reactive-extrusion process, it is desirable that the initiator generates free radicals through the application of heat. Such initiators are generally referred to as thermal initiators. For the initiator to function as a useful source of radicals for grafting, the initiator should be commercially and readily available, stable at ambient or refrigerated conditions, and generate radicals at reactive-extrusion temperatures.

Compounds containing an O—O, S—S, or N=N bond may be used as thermal initiators. Compounds containing O—O bonds, peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy) hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator. This invention has been demonstrated in the following Examples by the use of a liquid, organic peroxide initiator available from Elf Atochem North America, Inc. of Philadelphia, Pa., sold under the trade designation LUPERSOL® 101. LUPERSOL® 101 is a free radical initiator and comprises 2,5-dimethyl-2,5-di(t-butylperoxy) hexane. Other initiators and other grades of LUPERSOL® initiators may also be used, such as LUPERSOL® 130. Mixtures of various initiators or peroxides are desirable for tailoring and/or adjusting the reactive extrusion temperatures and conditions. The initiator is added to the poly(ethylene oxide) in a range of from about 1 weight percent to about 30 weight percent relative to the weight of the poly(ethylene oxide).

A variety of reaction vessels may be useful in the practice of this invention. The modification of the PEO resin can be performed in any vessel as long as the necessary mixing of PEO resin, the nonpolar monomer and the initiator is achieved and enough thermal energy is provided, to effect grafting. Suggested vessels include any suitable mixing device, such as Bradender Plasticorders, Haake extruders, single or multiple screw extruders, or any other mechanical mixing devices which can be used to mix, compound, process or fabricate polymers. In a desired embodiment, the reaction device is a counter-rotating twin-screw extruder, such as a Haake extruder available from Haake, 53 West Century Road, Paramus, N.J. 07652 or a co-rotating, twin-screw extruder, such as a ZSK-30 twin-screw, compounding extruder manufactured by Werner & Pfleiderer Corporation of Ramsey, N.J. It should be noted that a variety of extruders can be used to modify the PEO in accordance with the invention provided that mixing and heating occur.

The ZSK-30 extruder employed in the Examples allows multiple feeding, has venting ports and is capable of producing modified PEO at a rate of up to 50 pounds per hour. If a higher rate of production of modified PEO is desired, a commercial-scale extruder of a larger diameter may be used. The ZSK-30 extruder has a pair of co-rotating screws arranged in parallel with the center to center distance between the shafts of the two screws at 26.2 mm. The nominal screw diameters are 30 mm. The actual outer diameters of the screws are 30 mm and the inner screw diameters are 21.3 mm. The thread depths is 4.7 mm. The lengths of the screws are 1328 mm and the total processing section length was 1338 mm. This ZSK-30 extruder had 14 processing barrels, which are numbered consecutively 1 to 14 from the feed barrel to the die for the purposes of this disclosure. The first barrel, barrel #1, received the PEO and was not heated but cooled by water. The other thirteen barrels were heated. The other thirteen barrels are divided into seven heating zones. The heating elements for barrels 2, 3, and 4 were grouped as Zone 1, barrels 5 and 6 were coupled as Zone 2, barrels 7 and 8 were coupled as Zone 3, barrels 9 and 10 were coupled as Zone 4, barrels 11 and 12 were coupled as Zone 5, barrels 13 and 14 were coupled as Zone 6, and the die was Zone 7. In the Examples, the temperature of Zone 1 was set at 170° C., and the temperatures of Zones 2 through 7 were set at 180° C. The PEO resin feed rate was 25 lb/hr, fed to the extruder at the extruder feed throat. The screw speed of the extruder was set at 300 rpm.

The monomer employed in the examples, EHMA, was injected into barrel #5 and the initiator was injected into barrel #6. Both the monomer and the initiator were injected via pressurized nozzle injectors manufactured by Werner & Pfleiderer. The nozzle injectors produce a fine spray of monomer and initiator and ensure uniformity in the compositions. The order in which the PEO, monomer and initiator are added is not critical and the initiator and monomer may be added at the same time or separately. However, the addition order used in the Examples is desirable. The die used to extrude the modified PEO strands has four openings of 3 mm in diameter which are separated by 7 mm. Because the grafting of nonpolar monomer onto the PEO reduced the viscosity of the PEO so drastically, the PEO could not be cooled in strand form. Therefore, the modified PEO was instead collected on release paper as it exited the extruder and allowed to cool to room temperature. After cooling of the extruded PEO was complete, the modified PEO extrudates were chopped into small pieces, about an eighth to a quarter of an inch in equivalent circular diameter with a chipper or a grinder. In some instances, it may be desirable to chop or grind modified PEO extrudate under cryogenic conditions. The chopped pieces of modified PEO were then tested for adhesive properties. The results of the tests are presented below.

The adhesive compositions of the present invention may further comprise other desirable components. It is suggested that the adhesive composition may contain from 0 to 35 weight percent of a tackifier or mixture of tackifiers and from 0 to 35 weight percent of a wax or mixture of waxes. The wax can be hydrophilic or hydrophobic. The addition of tackifiers and waxes may be used to improve the properties, such as sprayability and melt processability, of the adhesives of the present invention. Hot-melt adhesives have a number of desired properties such as high tackiness and low melt viscosity when hot, so that the hot-melt adhesive can be easily applied to a substrate. The properties desired for hot-melt adhesives are not present in conventional PEO resins and PEO compositions, including PEO resin grafted with only polar monomers. It was surprisingly discovered that PEO resins grafted with nonpolar monomers do possess properties desirable for hot-melt and water-soluble adhesive applications.

Materials, substrates and articles to which the water-soluble adhesive compositions of the present invention can be applied include nonwoven, such as spunbond and melt-blown webs, films nonwoven laminates, plastics, and elastomers. The water-soluble adhesive compositions of the present invention and laminates comprising the water-soluble adhesive compositions of the present invention are useful in the manufacture of flushable personal care products such as diapers, feminine care products pantiliners, training pants, adult incontinence products and the like.

EXAMPLES

Table 1 shows a summary of five experimental runs made with two different PEO resins, EHMA as the nonpolar monomer and LUPERSOL® 101 as an initiator. The two PEO resins used in the examples were POLYOX® WSR-205 and WSR N-80 which have measured molecular weights of approximately 600,000 g/mol and 200,000 g/mol, respectively, as determined by Theological measurements. Both PEO resins were obtained in powder form from Union Carbide.

TABLE 1

| Example No. | Grade of PEO Resin POLYOX ® | PEO Resin Rate (lb/hr) | Monomer Rate (lb/hr) | Initiator Rate (lb/hr) |
|---|---|---|---|---|
| 1 | WSR-205 | 25 | 0.38 | 0.043 |
| 2 | WSR-205 | 25 | 0.65 | 0.050 |
| 3 | WSR-205 | 25 | 1.10 | 0.083 |
| 4 | WSR N-80 | 25 | 0.33 | 0.035 |
| 5 | WSR N-80 | 25 | 0.78 | 0.055 |

Process Observations and Adhesive Properties

During the reactive extrusion using the nonpolar monomer EHMA, it was surprisingly observed that the melt pressure on the extruder was extremely low, in the range of 10 to 30 psi. Typically, the melt pressure for grafting a polar monomer stays in the range of 600 to 900 psi. This reduction in the melt pressure is very dramatic. When the extrudate was tested, it was found that the viscosity of the extruded, nonpolar monomer grafted PEO copolymer was also extremely low. Because of the low viscosity, the nonpolar monomer grafted PEO resin could not be cooled in strand form. Instead the extrudate was collected on release paper as it exited the extruder. During the collection process the polymer was surprisingly observed to have tackiness and adhesiveness similar to that of a hot-melt adhesive.

In an effort to quickly assess the adhesive properties of the nonpolar monomer grafted PEO polymer, several pieces of a polar grafted PEO film, such as described in U.S. patent application Ser. No. 09/001,408 which is also herein incorporated by reference in its entirety, and polypropylene spunbond were bonded with the EHMA grafted PEO composition. The EHMA grafted PEO appeared to be capable of bonding both films and nonwoven materials. It was found that a strong bond was formed when two pieces of polar grafted PEO film were bonded together by the still warm, recently extruded, EHMA grafted PEO resin. When one of the bonded grafted PEO film composites was placed in water, the entire assembly dissolved.

When two pieces of polypropylene spunbond fabric were bonded together by this nonpolar monomer grafted PEO-based adhesive, a strong bond was also formed. The article of bonded fabric also separated once it was placed in water, leaving two independent pieces of free-flowing nonwoven fabric. These preliminary tests establish a basis for the use of the nonpolar monomer grafted PEO as water-soluble, water-responsive and water-soluble adhesive. Water-soluble, water-responsive and water-soluble adhesives are very useful for making flushable personal care products such as diapers, training pants, etc. and in making health care products, such as surgical gowns.

Applicability to Spraying Applications

One common method of applying adhesives is by spraying. Spraying requires very low viscosity material with good flow properties. The adhesive is typically heated and sprayed onto a substrate in its molten form. To determine the sprayability of one of the adhesive compositions of the present invention, an EHMA grafted PEO resin was placed in a PAM 600 Spraymatic adhesive spray gun that is commercially available from Fastening Technology, Inc. The spray gun was set at 149° C., approximately 90° C. higher than the melting temperature of the resin, to achieve a minimal viscosity level. The resin was allowed to melt and spraying was attempted. It was found that the resin was difficult to spray initially. The initial difficulty is probably due to the omission of additives such as waxes and plasticizers to the hot-melt adhesive resin. Additive, such as waxes and plasticizers, are usually compounded into adhesives to improve processability. Adjustment of temperature and pressure on the spray gun, however, made spraying possible. The viscosity of the adhesive and correspondingly the sprayability of the nonpolar monomer grafted PEO resins as hot-melt adhesives can be significantly improved by adding waxes and tackifiers normally incorporated in adhesive compositions.

Bond Strength

Figure 2:
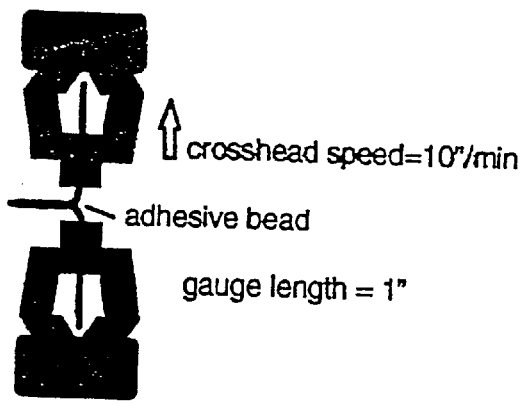
FIG. 2 illustrates the apparatus and method used to test the adhesive bond strength of the nonpolar monomer grafted poly(ethylene oxide) compositions.

Because the resin could not be easily sprayed uniformly, another method was devised to apply and test the bond strength of the EHMA grafted PEO resin. The PAM 600 Spraymatic adhesive gun was still used, but the pressure setting was decreased until a steady stream of adhesive exiting the gun could be obtained. The nonpolar monomer grafted PEO adhesive was applied to polypropylene spunbond in a bead form with minimal add on targeted. FIG. 1 illustrates a sample preparation and FIG. 2 illustrates the bond strength test set-up.

Samples were made with the resin from Example 2 of Table 1 and with a commercially available diaper construction adhesive obtained from National Starch, NAT 34-5610 construction adhesive. The load in grams required to separate the bonded samples was measured as the grips of the testing device moved apart. Table 2 summarizes the bond strength results for the nonpolar monomer grafted PEO adhesive of Example 2 and for NAT 34-5610 construction adhesive. NAT 34-5610 construction adhesive is not water soluble and therefore not useful for making flushable personal care products. In Table 2, the letter "a" is used to denote adhesive failure at peak load during testing and the letter "c" is used to denote cohesive failure of the tested nonwoven web at peak load.

TABLE 2

| | Example 2 | | | | | |
|---|---|---|---|---|---|---|
| | Estimated Add-On 0.00781 grams | | Estimated Add-On 0.00219 grams | | Estimated Add-On 0.00451 grams | |
| Sample Number | Peak Load | Failure Type | Peak Load | Failure Type | Peak Load | Failure Type |
| 1 | 933 g | c | 986 | c | 570 | c |
| 2 | 246 g | a | 944 | a | 427 | a |
| 3 | 444 g | a | 1388 | c | 687 | c |
| 4 | 1,086 g | c | 1111 | c | 734 | a |
| Average | 677 g | | 1,107 | | 60 | |

TABLE 2-continued

NAT 34-5610

| | Estimated Add-On 0.03 grams | | Estimated Add-On 0.0107 grams | | Estimated Add-On 0.0331 grams | |
|---|---|---|---|---|---|---|
| Sample Number | Peak Load | Failure Type | Peak Load | Failure Type | Peak Load | Failure Type |
| 1 | 1,313 | c | 1,308 | a | 1,224 | a |
| 2 | 1,067 | a | 914 | c | 978 | a |
| 3 | 1,179 | c | 838 | a | 1,148 | c |
| 4 | 1,087 | a/c | 1,067 | a | 1,148 | a |
| Average | 1,162 | | 1,031 | | 1,125 | |

Overall, the bond strength of the nonpolar monomer grafted PEO composition of Example 2 was lower and less consistent than that of the commercially available NAT 34-5610 adhesive. This may be due to the fact that the add-on level of Example 2 is significantly lower than the add-on level of NAT 34-5610 adhesive. The overall average peak load was 800 g for Example 2 and 1100 g for the NAT 34-5610 adhesive. The standard deviation of the twelve peak load values recorded for Example 2 was 336 compared to 146 for the NAT 4-5610 adhesive. However, it is important to note that a highly formulated, commercially available adhesive is being compared to straight EHMA-g-PEO polymer resin. That is, no additives were added to the EHMA-g-PEO resin of Example 2 that was tested. It is reasonable to deduce that the bond strength of the EHMA grafted PEO polymer can be increased with the addition of tackifiers. Additionally, it is reasonable to deduce that the consistency of the nonpolar monomer grafted PEO resin can be improved by the addition of conventional adhesives additives.

Melt Rheology

The Theological properties of the nonpolar monomer grafted PEO compositions were analyzed on a Goettfert Rheograph 2003 capillary melt rheometer. The test temperature was held constant at 180° C. and the apparent shear rates were varied from 50 s$^{-1}$ to 1000 s$^{-1}$. A 500 bar transducer was used to measure pressure, and the resin was allowed to melt for 4 minutes before the test began. The melt rheology data for Examples 1–5 is provided in Table 3. From the data, it is observed that as the amount of nonpolar monomer grafted onto the PEO resin during reactive extrusion increased the apparent viscosity of the PEO decreased.

TABLE 3

| Example No. | Apparent Shear Viscosity (Pa · s) at | | | | |
|---|---|---|---|---|---|
| | 50 s$^{-1}$ | 100 s$^{-1}$ | 200 s$^{-1}$ | 500 s$^{-1}$ | 1000 s$^{-1}$ |
| 1 | 158.8 | 132.3 | 126.2 | 98.5 | 78.8 |
| 2 | 101.8 | 67.2 | 61.1 | 41.9 | |
| 3 | 44.8 | 67.2 | 48.9 | 41.9 | |
| 4 | 16.3 | 22.4 | 22.4 | 28.9 | |
| 5 | 12.2 | 14.2 | 15.3 | 14.7 | 10.6 |

DSC Analysis of Thermal Properties

Examples 1–5 were also analyzed by Differential Scanning Calorimetry (DSC) to determine differences in thermal properties. Table 4 lists the melting peak temperature ($T_m$) and enthalpy of melting value ($\Delta H$) for each of the tested resin samples.

TABLE 4

| Example No. | Melting Peak $T_m$ (° C.) | Enthalpy of Melting $\Delta H$ |
|---|---|---|
| 1 | 64.5 | 139.7 |
| 2 | 65.5 | 137.2 |
| 3 | 65.8 | 152.2 |
| 4 | 66.0 | 152.9 |
| 5 | 65.4 | 148.3 |

The present invention has been illustrated in great detail by the above specific Examples. It is to be understood that these Examples are illustrative embodiments and that this invention is not to be limited by any of the Examples or details in the Description. Those skilled in the art will recognize that the present invention is capable of many modifications and variations without departing from the scope of the invention. Accordingly, the Detailed Description and Examples are meant to be illustrative and are not meant to limit in any manner the scope of the invention as set forth in the following claims. Rather, the claims appended hereto are to be construed broadly within the scope and spirit of the invention.

What is claimed is:

1. A thermoplastic, water-soluble, hot-melt adhesive composition comprising a backbone of a polymer of ethylene oxide and side chains of a grafted nonpolar monomer produced by the melt extrusion of a polymer of ethylene oxide and the nonpolar monomer wherein the nonpolar monomer is selected from styrene and a monomer comprising one or more alkyl groups or cycloalkyl groups and the nonpolar monomer comprise three or more carbon atoms, wherein the graft copolymer of ethylene oxide is formed by the reactive extrusion of a homopolymer of ethylene oxide, 0.1 to 20 weight percent of an nonpolar monomer or a mixture of monomers comprising a nonpolar monomer and 0.1 to about 30 weight percent of a free radical initiator relative to the weight of homopolymer of ethylene oxide.

2. The thermoplastic, water-soluble, hot-melt adhesive composition of claim 1, wherein the nonpolar monomer is selected from the group consisting of $C_3$ to $C_{20}$ alkyl and cycloalkyl acrylates and $C_3$ to $C_{20}$ alkyl and cycloalkyl methacrylates.

3. The thermoplastic, water-soluble, hot-melt adhesive composition of claim 1, wherein the nonpolar monomer is selected from the group consisting of methyl acrylate, ethyl acrylate, propyl acrylate, isopropyl acrylate, butyl acrylate, n-butyl acrylate, sec-butyl acrylate, tert-butyl, pentyl acrylate, hexyl acrylate, 2-ethylhexyl acrylate, heptyl acrylate, octyl acrylate, nonyl acrylate, decyl acrylate, undecyl acrylate, dodecyl acrylate, tridecyl acrylate, tetradecyl acrylate, pentadecyl acrylate, hexadecyl acrylate, heptadecyl acrylate, octadecyl acrylate, methyl methacrylate, ethyl methacrylate, propyl methacrylate, isopropyl methacrylate, butyl methacrylate, n-butyl methacrylate, sec-butyl methacrylate, tert-butyl, pentyl methacrylate, hexyl methacrylate, 2-ethylhexyl methacrylate, heptyl methacrylate, octyl methacrylate, nonyl methacrylate, decyl methacrylate, undecyl methacrylate, dodecyl methacrylate, tridecyl methacrylate, tetradecyl methacrylate, pentadecyl methacrylate, hexadecyl methacrylate, heptadecyl methacrylate, octadecyl methacrylate and styrene.

4. The thermoplastic, water-soluble, hot-melt adhesive composition of claim 1, wherein the nonpolar monomer is 2-ethylhexyl methacrylate.

5. The thermoplastic, water-soluble, hot-melt adhesive composition of claim 1, wherein the graft copolymer of ethylene oxide and a nonpolar monomer comprises a backbone of poly(ethylene oxide) and side branches comprising units of the grafted nonpolar monomer or a mixture of grafted nonpolar monomers.

6. The thermoplastic, water-soluble, hot-melt adhesive composition of claim 1, wherein the graft copolymer of ethylene oxide and a nonpolar monomer comprises a backbone of a polymer of ethylene oxide and side branches comprising units of a grafted $C_3$ to $C_{20}$ alkyl (meth)acrylate.

7. The thermoplastic, water-soluble, hot-melt adhesive composition of claim 1, wherein the graft copolymer of ethylene oxide and a nonpolar monomer comprises a backbone of poly(ethylene oxide) and grafted side branches comprising units selected from the group of propyl acrylate, butyl acrylate, isopropyl acrylate, pentyl acrylate, hexyl acrylate, 2-ethylhexyl acrylate, octyl acrylate, propyl methacrylate, butyl methacrylate, isopropyl methacrylate, pentyl methacrylate, hexyl methacrylate, 2-ethylhexyl methacrylate, octyl methacrylate and mixtures thereof.

8. The thermoplastic, water-soluble, hot-melt adhesive composition of claim 1, wherein the graft copolymer of ethylene oxide and a nonpolar monomer comprises a backbone of poly(ethylene oxide) and side branches comprising grafted 2-ethylhexyl methacrylate.

9. A flushable article comprising the thermoplastic, water-soluble, hot-melt adhesive composition of claim 1.

10. A water-soluble graft copolymer comprising a backbone of a polymer of ethylene oxide and side chains of a grafted nonpolar monomer produced by the melt extrusion of a polymer of ethylene oxide and the nonpolar monomer in the presence of 0.1 to about 20 weight percent of a free radical initiator relative to the weight of homopolymer of ethylene oxide, wherein the nonpolar monomer is selected from styrene and a monomer comprising one or more alkyl groups or cycloalkyl groups and the nonpolar monomer comprise three or more carbon atoms, wherein the poly(ethylene oxide) has an average molecular weight ranging from about 100,000 g/mol to about 8,000,000 g/mol. and wherein the side chains of a grafted nonpolar monomer comprise 0.1 weight percent to about 20 percent of the weight of the graft copolymer.

11. The graft copolymer of claim 10, wherein the nonpolar monomer is selected from the group of $C_3$ to $C_{20}$ alkyl acrylates, $C_3$ to $C_{20}$ cycloalkyl acrylates, $C_3$ to $C_{20}$ alkyl methacrylates, $C_3$ to $C_{20}$ cycloalkyl methacrylates and mixtures thereof.

12. The graft copolymer of claim 10, wherein the grafted nonpolar monomer is selected from the group consisting of methyl acrylate, ethyl acrylate, propyl acrylate, isopropyl acrylate, butyl acrylate, n-butyl acrylate, sec-butyl acrylate, tert-butyl, pentyl acrylate, hexyl acrylate, 2-ethylhexyl acrylate, heptyl acrylate, octyl acrylate, nonyl acrylate, decyl acrylate, undecyl acrylate, dodecyl acrylate, tridecyl acrylate, tetradecyl acrylate, pentadecyl acrylate, hexadecyl acrylate, heptadecyl acrylate, octadecyl acrylate, methyl methacrylate, ethyl methacrylate, propyl methacrylate, isopropyl methacrylate, butyl methacrylate, n-butyl methacrylate, sec-butyl methacrylate, tert-butyl, pentyl methacrylate, hexyl methacrylate, 2-ethylhexyl methacrylate, heptyl methacrylate, octyl methacrylate, nonyl methacrylate, decyl methacrylate, undecyl methacrylate, dodecyl methacrylate, tridecyl methacrylate, tetradecyl methacrylate, pentadecyl methacrylate, hexadecyl methacrylate, heptadecyl methacrylate, octadecyl methacrylate and styrene.

13. The graft copolymer of claim 10, wherein the nonpolar monomer is 2-ethylhexyl methacrylate.

14. The graft copolymer of claim 10, wherein the graft copolymer comprises a backbone of poly(ethylene oxide) and side branches comprising units of the grafted nonpolar monomer.

15. The graft copolymer of claim 10, wherein the graft copolymer of comprises a backbone of polymer of ethylene oxide and side branches comprising units of a grafted $C_3$ to $C_{20}$ alkyl acrylates and $C_3$ to $C_{20}$ alkyl methacrylates.

16. The graft copolymer of claim 10, wherein the graft copolymer comprises a backbone of poly(ethylene oxide) and side branches comprising grafted units selected from the group of propyl acrylate, butyl acrylate, isopropyl acrylate, pentyl acrylate, hexyl acrylate, 2-ethylhexyl acrylate, octyl acrylate, propyl methacrylate, butyl methacrylate, isopropyl methacrylate, pentyl methacrylate, hexyl methacrylate, 2-ethylhexyl methacrylate, octyl methacrylate and mixtures thereof.

17. The graft copolymer of claim 10, wherein the graft copolymer comprises a backbone of poly(ethylene oxide) and side branches comprising grafted 2-ethylhexyl methacrylate.

18. An article comprising the graft copolymer of claim 10.

19. A water-soluble graft copolymer comprising a backbone of a polymer of ethylene oxide and side chains of a grafted nonpolar monomer, wherein the nonpolar monomer comprises one more alkyl groups or cycloalkyl groups and the alkyl groups or cycloalkyl comprise three or more carbon atoms, wherein the side chains of a grafted nonpolar monomer comprise 0.1 weight percent to about 20 percent of the weight of the graft copolymer.

20. A method of making a graft copolymer of ethylene oxide and a nonpolar monomer comprising:
   continuously adding a poly(ethylene oxide), 0.1 to about 30 weight percent of a free radical initiator and 0.1 to 20 weight percent of a nonpolar monomer or a mixture of monomers comprising a nonpolar monomer relative to the weight of homopolymer of ethylene oxide into an extruder under melt conditions without a solvent, wherein the poly(ethylene oxide) has an average molecular weight ranging from about 100,000 g/mol to about 8,000,000 g/mol; and
   mixing the poly(ethylene oxide), the initiator and the nonpolar monomer under conditions sufficient to graft the nonpolar monomer onto the poly(ethylene oxide) and form a thermoplastic, water-soluble graft copolymer of ethylene oxide.

21. The method of claim 20, wherein the nonpolar monomer is selected from the group of $C_3$ to $C_{20}$ alkyl acrylates and $C_3$ to $C_{20}$ alkyl methacrylates.

22. The method of claim 20, wherein the graft copolymer comprises a backbone of poly(ethylene oxide) and side branches comprising grafted units selected from the group of propyl acrylate, butyl acrylate, isopropyl acrylate, pentyl acrylate, hexyl acrylate, 2-ethylhexyl acrylate, octyl acrylate, propyl methacrylate, butyl methacrylate, isopropyl methacrylate, pentyl methacrylate, hexyl methacrylate, 2-ethylhexyl methacrylate, octyl methacrylate and mixtures thereof.

23. A method of making a graft copolymer of ethylene oxide and a nonpolar monomer comprising:
   adding a poly(ethylene oxide), an initiator and a nonpolar monomer into an extruder under melt conditions without a solvent, wherein the nonpolar monomer is added to the poly(ethylene oxide) in a range of from about 0.1 weight percent to about 20 weight percent relative to the weight of the poly(ethylene oxide); and
   mixing the poly(ethylene oxide), the initiator and the nonpolar monomer under conditions sufficient to graft the nonpolar monomer onto the poly(ethylene oxide) and form a thermoplastic, water-soluble graft copolymer of ethylene oxide.

24. The method of claim 23, wherein the nonpolar monomer is selected from the group of $C_3$ to $C_{20}$ alkyl acrylates and $C_3$ to $C_{20}$ alkyl methacrylates.

25. The method of claim 23, wherein the graft copolymer comprises a backbone of poly(ethylene oxide) and side branches comprising grafted units selected from the group of propyl acrylate, butyl acrylate, isopropyl acrylate, pentyl acrylate, hexyl acrylate, 2-ethylhexyl acrylate, octyl acrylate, propyl methacrylate, butyl methacrylate, isopropyl methacrylate, pentyl methacrylate, hexyl methacrylate, 2-ethylhexyl methacrylate, octyl methacrylate and mixtures thereof.

26. A method of making a graft copolymer of ethylene oxide and a nonpolar monomer comprising:

adding a poly(ethylene oxide), an initiator and a nonpolar vinyl monomer into an extruder under melt conditions without a solvent, wherein the initiator is added to the poly(ethylene oxide) in a range of from about 1 weight percent to about 30 weight percent relative to the weight of the poly(ethylene oxide); and mixing the poly(ethylene oxide), the initiator and the nonpolar vinyl monomer under conditions sufficient to graft the nonpolar vinyl monomer onto the poly(ethylene oxide) and form a thermoplastic, water-soluble graft copolymer of ethylene oxide.

27. The method of claim 26, wherein the nonpolar monomer is selected from the group of $C_3$ to $C_{20}$ alkyl acrylates and $C_3$ to $C_{20}$ alkyl methacrylates.

28. The method of claim 26, wherein the graft copolymer comprises a backbone of poly(ethylene oxide) and side branches comprising grafted units selected from the group of propyl acrylate, butyl acrylate, isopropyl acrylate, pentyl acrylate, hexyl acrylate, 2-ethylhexyl acrylate, octyl acrylate, propyl methacrylate, butyl methacrylate, isopropyl methacrylate, pentyl methacrylate, hexyl methacrylate, 2-ethylhexyl methacrylate, octyl methacrylate and mixtures thereof.

* * * * *